(12) United States Patent
Lähteenmäki

(10) Patent No.: US 6,728,564 B2
(45) Date of Patent: Apr. 27, 2004

(54) CONFIGURABLE SENSOR SYSTEM FOR MEASURING BIOPOTENTIALS

(75) Inventor: Markku Lähteenmäki, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/898,603

(22) Filed: Jul. 3, 2001

(65) Prior Publication Data

US 2003/0009096 A1 Jan. 9, 2003

(51) Int. Cl.[7] ............... A61B 5/0478; A61B 5/0492
(52) U.S. Cl. .............. 600/383; 600/393; 600/544; 600/546; 600/547; 128/902
(58) Field of Search ................. 600/383, 393, 600/544–547; 128/902

(56) References Cited

U.S. PATENT DOCUMENTS

| | | |
|---|---|---|
| 4,112,930 A | 9/1978 | Feldman et al. |
| 4,359,724 A * | 11/1982 | Zimmerman et al. ....... 600/383 |
| 4,595,013 A * | 6/1986 | Jones et al. ................. 600/383 |
| 4,638,807 A * | 1/1987 | Ryder ......................... 600/383 |
| 4,850,367 A * | 7/1989 | Rantala ...................... 600/483 |
| 5,231,990 A | 8/1993 | Gauglitz |
| 5,265,607 A | 11/1993 | Moberg |
| 5,305,746 A | 4/1994 | Fendrock |
| 5,813,404 A | 9/1998 | Devlin et al. |
| 6,032,064 A | 2/2000 | Devlin et al. |
| 6,032,072 A | 2/2000 | Greenwald et al. |
| 2002/0019588 A1 * | 2/2002 | Marro et al. ................ 600/383 |

FOREIGN PATENT DOCUMENTS

EP          008846          3/1980

* cited by examiner

*Primary Examiner*—Lee Cohen
(74) *Attorney, Agent, or Firm*—Andrus, Sceales, Starke & Sawall, LLP

(57) ABSTRACT

A configurable system for obtaining a measurement of activity producing biopotentials in a subject, for example EEG or EMG biopotentials. The system includes a three electrode array positionable on the head of the patient to detect signals generated in the head of the subject. The array is connected to a monitor that includes a switch arrangement that is selectively configurable to direct the incoming signals received by the electrode array to specified inputs of a differential amplifier that creates signals that are displayed on the monitor. The switch arrangement is configurable to measure the activity of the subject in a conventional 1-channel measurement mode. The switch arrangement can also be configured to simulate a 2-channel measurement mode by alternating the configuration of the switch arrangement in a pre-determined manner.

28 Claims, 2 Drawing Sheets

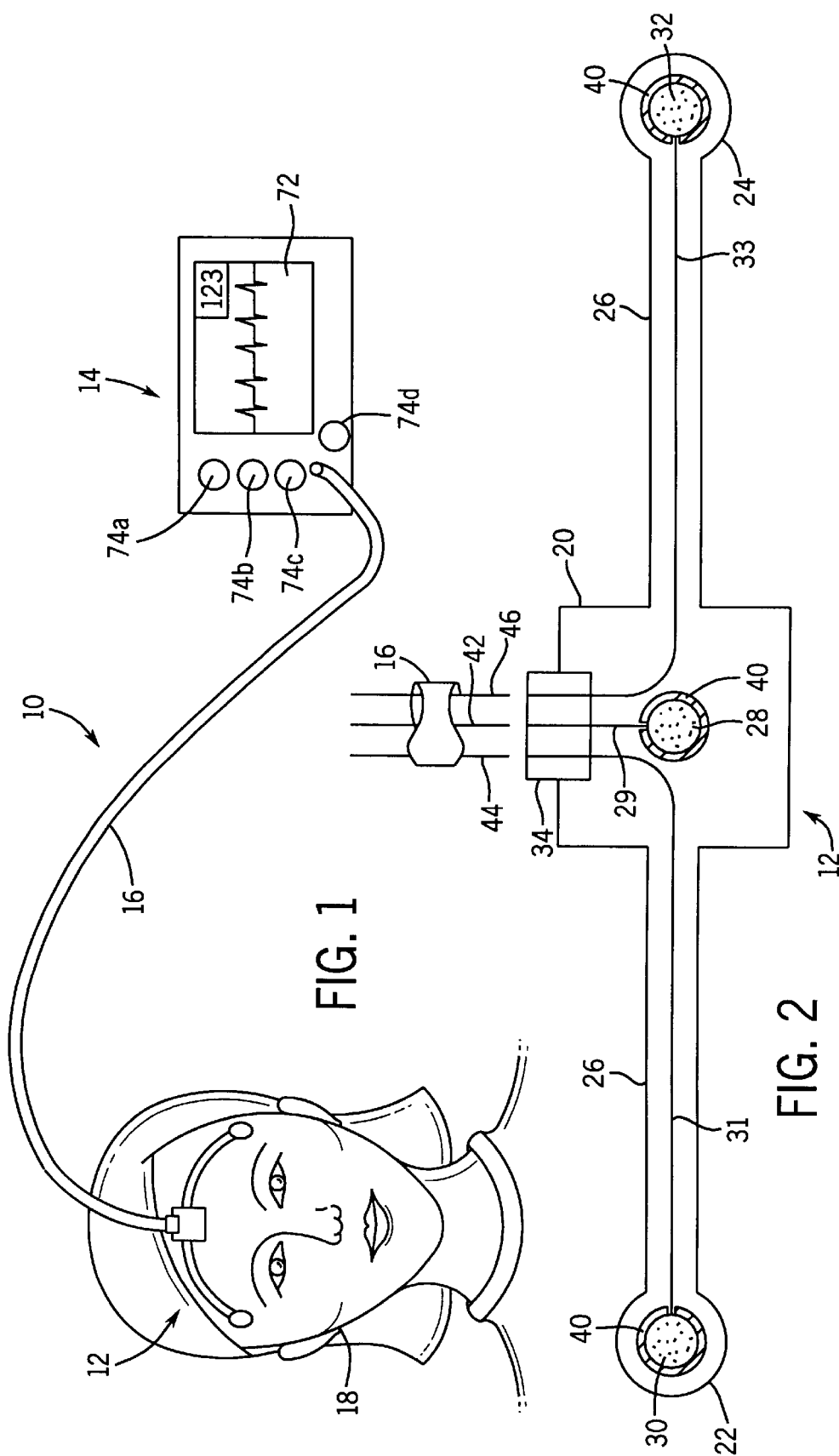

CONFIGURABLE SENSOR SYSTEM FOR MEASURING BIOPOTENTIALS

FIELD OF THE INVENTION

The present invention relates to an apparatus and method for measuring the biopotential signals produced in a subject, and more specifically to an apparatus and method that is configurable to provide either a 1-channel operating mode or a mode resembling 2-channel operation.

BACKGROUND OF THE INVENTION

Electroencephalography (EEG) is a well established method for assessing the brain function by picking up the weak biosignals generated in the brain with electrodes on the skull surface. To obtain the biosignals, multiple electrodes are placed on the scalp of a patient in accordance with a recognized protocol. EEG has been in wide use for decades in basic research of the neural system of brain as well as clinically in diagnosis of various neurophysiological disorders.

The EEG signals received by the electrodes from the scalp are amplified by amplifiers which may be of the differential type to minimize electrical interference. Each amplifier has three inputs: 1) a positive signal input; 2) a negative signal input; and 3) a ground input. Consequently, even the most rudimentary 1-channel EEG measurement procedure requires the use of three electrodes. Applying electrodes to the scalp takes time and skill, requires skin preparation, e.g., removal of hair, and is especially difficult in a thick hair environment.

One of the special applications for EEG which has received much attention to during the 1990's is use of a processed EEG signal for objective quantification of the amount of brain activity for the purpose of determining the level of consciousness of a patient. In its simplest form, this usage of EEG allows for the automatic detection of the alertness of an individual, i.e. if he or she is awake or asleep. This has become a significant issue, both scientifically and commercially, in the context of measuring the depth of unconsciousness induced by anesthesia during surgery. Modern anesthesia practices use a sophisticated balancing technique with a combination of drugs for maintaining adequate hypnosis, analgesia, muscle relaxation, and/or suppression of the autonomic nervous system and blockage of the neuromuscular junction. The need for a reliable system for the monitoring of the adequacy of the anesthesia is based on both safety and economical concerns. An anesthesia dose which is too light can, in the worst case, can cause the patient to wake up in the middle of the operation and create a highly traumatic experience both for the patient and for the personnel administering the anesthesia. At the opposite extreme, the administration of too much anesthesia generates increased costs due to the excessive use of anesthesia drugs and the time needed to administer the drugs. Over dosage of anesthesia drugs also affects the quality and length of the postoperative period immediately after the operation and the time required for any long term post-operative care.

A significant main advancement in making the EEG-based measurement of the depth of unconsciousness induced by anesthesia an easy-to-use, routine procedure was a finding based on Positron Emission Tomography (PET) that determined that the effects of the anesthetic drugs on the brain are global in nature. This means that for many applications it is enough to measure the forebrain or frontal cortex EEG from the forehead of the subject. The forehead is both an easy to access and is a hairless location on the subject. Electrodes placed with an appropriate spacing between electrodes on the forehead can pick up an adequate signal originating from the anterior cortex in the brain. This discovery, together with development of a special algorithm, namely, the Bispectral Index (BIS), an electrode design requiring no skin preparation, as disclosed in U.S. Pat. No. 5,305,746, incorporated herein by reference, and a convenient integrated electrode array, as disclosed in U.S. Pat. No. 6,032,064, also incorporated herein by reference, have contributed to a viable commercial product manufactured and sold by Aspect Medical of Natick, Mass. capable of obtaining a measurement of the state or activity of the brain during delivery of anesthesia using an EEG system.

The '064 patent teaches a disposable EEG electrode array. One array has three electrodes for 1-channel measurement. A different array has four electrodes for 2-channel measurements. The 2-channel set-up is symmetrical in configuration and separately collects the signals between the mid-forehead and left and right mastoidal points, respectively. The 2-channel measurement configuration is used to determine the differences in the EEG signal in situations in which the right and left frontal hemispheres might be expected to produce different EEG signals. This can be caused, for example, by ischemia or burst suppression, i.e., EEG signals in discontinuous bursts, in either of the sides of the head, as well as artifacts in the EEG signals due to movement of the eyes of the subject or poor contact in one of the electrodes.

However, if it is desired to switch from 1-channel to 2-channel EEG measurements, with these prior art sensors it is necessary to remove the three electrode, 1-channel sensor and replace it with a four electrode, 2-channel sensor, and vice versa. This requires significant time and effort on the part of the technician taking the measurements as the first sensor must be removed before the second sensor can be positioned on the individual, and because the positioning of the second sensor must be precise in order to obtain an accurate measurement of the neurological activity of the subject.

It would, therefore, be desirable to develop a neurological activity sensor system which is capable of operation in both a 1-channel and 2-channel manner to obtain EEG measurements of the neurological activity of the subject. The sensor system should have as simple a construction as possible to minimize the amount of time and effort necessary to properly position the electrodes of the sensor on the subject prior to obtaining the measurements.

While the foregoing has discussed the use of EEG signals, it may also be desirable to obtain electromyographic (EMG) signals arising from the forehead of the subject. Should an anesthetized patient approach a state of consciousness, the frontalismuscle in the forehead of the subject may contract from a pain sensation or for other reasons. When sensed by appropriately placed electrodes, this muscle activity can provide an early indication that the subject is emerging from anesthesia.

SUMMARY OF THE INVENTION

It is, therefore, an object of the present invention to provide a low cost sensor system of simple construction having an electrode array with three basic EEG electrodes capable of performing measurements of neurological activity in different portions of the brain, such as the overall frontal cortex of the brain or the left or right hemispheres of the forebrain.

A further object of the invention is to provide a sensor system capable of obtaining EMG signals from the head of a subject.

It is another object of the invention to provide a sensor system and method of operating same which can be configured to selectively operate in a conventional 1-channel mode or in a manner to approximate a 2-channel measurement.

It is still a further object of the invention to provide a sensor system wherein the electrode array is manufactured to be disposable.

The invention employs an electrode array of three electrodes. The sensor system uses a switching arrangement connected to the electrode array to route signals from each of three electrodes forming the array in a manner that allows measurement of the biopotential difference between any pair of the three electrodes of the system while using the remaining electrode in each case as a ground electrode. To this end, a signal from each of the three electrodes can be selected by the switching arrangement for use as a positive input signal, a negative input signal or a ground signal to a signal processing unit, such as a differential amplifier to obtain a biopotential difference used to measure the neurological or muscular activity of the subject.

The switching arrangement can route the signals from the electrodes to form a 1-channel measurement mode to monitor the neurological activity of either the left or right hemisphere of the forebrain or overall frontal cortex of the brain. The switching arrangement can also route signals from selected pairs of electrodes to the differential amplifier in a pre-determined, alternating fashion to provide an essentially 2-channel measurement of neurological activity. EMG signal data is obtained in an analogous manner.

The sensor system and method of the present invention have significant advantages compared to a fixed 1-channel set-up. First of all, the system allows for the optimization of the signal quality regarding the signal-to-noise ratio in the signals of the electrode array. The system can automatically choose to start a measurement using the electrode on the frontal hemisphere that is receiving the strongest signal and/or the least amount of noise by sampling the signals and noise levels generated by each frontal hemisphere and received by each electrode prior to starting any measurement. Secondly, by switching 1-channel measurements using selected pairs of electrode signals back and forth in a predetermined sequence, this system can also work as a surrogate for a true 2-channel measurement system. The system can also be configured to monitor the status of the electrodes, and detect the origin of any interference or signal artifacts and for the diagnosis of any physiological changes that generate lateral asymmetry in the frontal cortex neural activity, such as changes in blood flow in one of the carotid arteries.

BRIEF DESCRIPTION OF THE DRAWINGS

The following drawings illustrate the best mode currently contemplated of practicing the present invention.

In the drawings:

FIG. 1 is a perspective view of the sensor system for measuring biopotentials constructed according to the present invention and connected to a subject;

FIG. 2 is a plan view of the electrode array of the system of FIG. 1; and

DETAILED DESCRIPTION OF THE INVENTION

Figure 3:
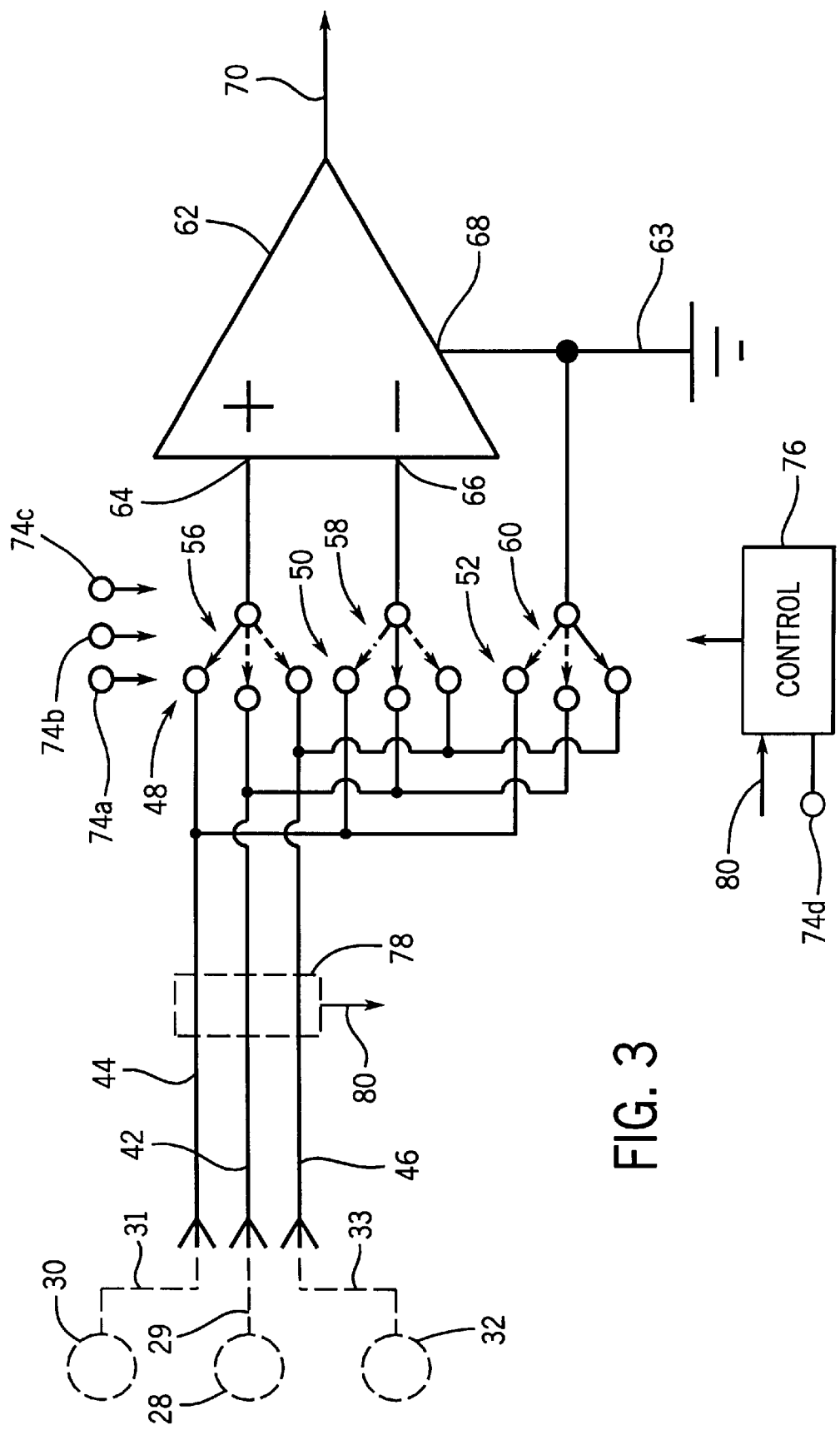
FIG. 3 is a schematic view of the circuitry used in the system of FIG. 1 to direct input signals from the electrodes to signal processing unit inputs for measurement of signal differences between different selected pairs.

With reference now to the drawings in which like reference numerals designate like parts throughout the disclosure, the sensor measurement system of the present invention is indicated generally at 10 in FIG. 1. The system 10 includes an electrode array 12 connected to a monitor 14 by a cable 16. The array 12 transmits neurological activity signals received from the forehead 18 of the patient to the monitor 14 which carries out signal processing and numerically or graphically displays EEG or EMG data. The data may also be stored for future use.

As best shown in FIGS. 1 and 2, the electrode array 12 includes a central body 20 and a pair of side bodies 22 and 24 connected to the central body 20 by a pair of flexible arms 26. The central body 20, side bodies 22 and 24 and arms 26 are each formed of a flexible, resilient material which enables the arms 26 to flex with respect to the central body 20. This allows the array 12 to conform to the shape of the subject's head 18 and to have the side bodies 22 and 24 positioned at the optional sites on the head 18 to detect activity producing biopotentials. The positioning of the array is shown generally in FIG. 1. The preferred material used in the construction of the electrode array 12 is a thermoplastic material, which also allows the electrode array 12 to be formed as a single unit, if desired, as shown in FIG. 1.

Each of the central body 20 and side bodies 22 and 24 includes an electrode 28, 30 and 32, respectively, disposed on one side of the electrode array 12. Each electrode 28, 30 and 32 is connected to a conductor 29, 31 and 33, respectively, that transmits biopotential signals received by the electrodes 28, 30 and 32 from the forehead 18. The electrodes and conductors are formed of a conductive material suitable for receiving and transmitting biopotentials, such as metallic foils or wires, vapor deposited or printed metallic layers, or the like. The electrodes 28, 30 and 32 and associated conductors 29, 31 and 33 are preferably formed on one side of the flexible, resilient material of array 12. However, the electrodes and conductors may also be formed separately from the array 12 and individually placed on the array 12 in a necessary configuration and location.

The conductors 31 and 33 extend from each of the electrodes along the arms 26 and are connected, along with conductor 29, to a connector 34 disposed on the central body 20. The connector 34 is used to connect the cable 16 to the electrode array 12 and is formed as one half of a conventional electrical connection, such as a male or female plug portion. Preferably, the connector 34 is formed as a female plug portion including an aperture (not shown) for the reception of a male plug portion (not shown) located on the end of the cable 16 extending away from monitor 14. The aperture exposes the end of each of the conductors 29, 31 and 33 leading from the electrodes 28, 30 and 32, respectively, such that the plug can contact the conductors and receive a biopotential signal transmitted by the conductors 29, 31 and 33 from the electrodes 28, 30 and 32, respectively, for transmission along the cable 16 to the monitor 14.

The array 12 also includes adhesive material 40 disposed on each of the central body 20 and side bodies 22 and 24, around the electrodes 28, 30 and 32. The material 40 functions to secure the array 12 and each electrode 28, 30 and 32 against the skin of the forehead 18 of the subject so that biopotential signals from the forehead 18 can be picked up by the electrodes 28, 30 and 32. The material 40 also prevents the movement of the array 12 and electrodes 28, 30 and 32 with respect to the forehead 18 to insure the electrodes remain in optimal locations on the forehead 18 for picking up the desired signals from the brain or head. The overall construction of the array 12 enables the array 12 to be disposed of in its entirety after use for measuring biopotential signals from the forehead 18 of a subject.

Referring now to FIGS. 1 and 3, the monitor 14 receives the signals picked up from the subject's head 18 by the electrodes 28, 30 and 32 via the cable 16. The cable 16 includes three input signal leads 42, 44 and 46 which extend along the cable 16 and each correspond to and connect with one of the conductors 29, 31 or 33 in the connector 34 via the male plug portion. At the end of cable 16, opposite the male plug portion, each lead 42, 44 and 46 is connected into a set of nodes 48, 50 and 52, respectively. The nodes 48, 50 and 52 form part of a switching arrangement which includes three switches 56, 58 and 60. Each switch 56, 58 and 60 is associated with one set of nodes 48, 50 and 52, respectively, such that each switch can selectively contact each of the three nodes in each set. The switches are shown schematically in the drawing for illustrative purposes and may comprise solid state switching elements or other suitable components.

The outputs of switches 56, 58 and 60 are connected to the inputs of a signal processing unit, shown as differential amplifier 62 which amplifies the biopotential signals transmitted from the leads 42, 44 and 46. For a signal processing unit comprising a differential amplifier, the output of switch 56 is connected to a positive signal input 64 of amplifier 62, the output of switch 58 is connected to a negative signal input 66, and the output of switch 60 is connected to a ground input 68 via ground 63. The signals transmitted to the positive signal input 64 and negative signal input 66 are used to establish a signal difference that is amplified by the differential amplifier 62 to create an output signal in conductor 70 which is processed and used to drive a display 72 for the monitor 14.

The monitor 14 also includes a plurality of buttons 74a, b, c, and d disposed on monitor 14. The buttons 74 are operably engaged with the switching arrangement and are used to control the configuration of the switches 56, 58 and 60 in order to alter the connections between the signal leads 42, 44, and 46 and amplifier 62. For EEG signals, this obtains various EEG measurements from the signals from the frontal cortex of the subject's forehead 18 or different sections thereof, which are displayed on the monitor 14.

To operate system 10, the cable 16 is connected to the electrode array 12 which is positioned on the subject's forehead 18 with each electrode 28, 30 and 32 in a desired location and secured to the patient's forehead by the adhesive material 40. By operating one of the buttons 74a, b, or c, the user selects the configuration of the switches 56, 58 and 60 within the monitor 14. The configuration of the switches determines how the biopotential signals obtained by the electrodes 28, 30 and 32 from the subject's forehead 18 will be utilized by differential amplifier 62. For example, when the switches 56, 58 and 60 are in the configuration shown in FIG. 3, the signal from the electrode 30 is utilized as the positive signal input 64, the signal from the electrode 28 is utilized as the negative signal input 66, and the signal from the electrode 32 is utilized as the ground input 68. For EEG signals, this would measure the biopotential signal existing in one of the hemispheres of the patient's forebrain, i.e. the right hemisphere shown in FIGS. 1 and 2. By operating a different button 74, the configuration of the switches 56, 58 and 60 will change such that signals from different electrodes 28, 30 and 32 will be utilized as the positive signal input 64, negative signal input 66 and ground input 68 for the amplifier 62 to measure the biopotential signal existing in the other forebrain hemisphere or in the overall frontal cortex of the brain. Thus by changing the configuration of the switches with buttons 74a, 74b, or 74c, and hence the inputs to differential amplifier 62, a user can determine the neurological activity in the right hemisphere of the forebrain, in the left hemisphere of the forebrain, or in the overall frontal cortex pursuant to an EEG measurement performed in the conventional 1-channel mode of the system 10.

Further, monitor 14 can contain a control 76 such that when button 74d is operated, a computer program or other control element, is initiated to periodically alternate the configuration of the switches 56, 58 and 60 in a specified manner. This allows the monitor 14 and system 10 to alternately measure the neurological activity in each hemisphere of the forebrain to obtain a measurement similar to that of a 2-channel EEG measurement mode. Thus, the system 10 can be selectively operated in either a selected 1-channel or 2-channel surrogate measurement mode simply by operating the appropriate button 74 on the monitor 14 associated with the desired measurement mode.

Operation of system 10 to obtain EMG biopotential signals is carried out in a manner analogous to that described above in connection with obtaining EEG signals.

By sensing properties such as the signal strength and/or signal noise in conductors 42, 44, and 46, as by signal sensor 78 and connection 80, control 76 can be used to provide signals of highest quality to differential amplifier 62, thereby to improve the quality of the output signal in conductor 70. Signal sensor 78 may also be used to provide and indication of the status of the electrodes of array 12.

Various alternatives are contemplated as being within the scope of the following claims particularly pointing out and distinctly claiming the subject matter regarded as the invention.

I claim:

1. A configurable sensor system for obtaining biopotential signals from the head of a subject, said system being adapted for use with a three electrode array positioned on the head of the subject, said sensor system comprising:
   a) a connection means adapted to be connected to the three electrode array for receiving electrical signals from the head transmitted through the array;
   b) a switch arrangement having a plurality of switching elements, said switching elements having inputs operably connected to the connection means and being adapted to be connected to each of the electrodes of the array via said connection means, each of said switching elements having an output; and
   c) a signal processing unit having a first signal input, a second signal input and a third input, said unit having an output providing an output signal,
   the switch arrangement being configured to selectively direct a different one of the electrical signals of the electrode array from the outputs of said switching elements to one of the first, second, and third inputs of the signal processing unit.

2. The system of claim 1 further defined as an EMG sensor for obtaining biopotential signals arising from muscle activity of the subject and wherein said connection means receives electrical signals from the muscles in the head of the subject transmitted through the array.

3. The system of claim 1 or 2 wherein the switch arrangement is capable of directing the signals from the electrode array to the first, second, and third inputs in a configuration to obtain signals from a selected portion of the head of the subject.

4. The system of claim 1 or 2 wherein the switch arrangement is capable of directing the signals from the electrode array to the inputs of the signal processing unit in a configuration to obtain biopotential signals from an enlarged area of the head of the subject.

5. The system of claim 1 or 2 wherein the switch arrangement includes control means for operating the switching arrangement to alternately direct the signals from the electrode array to the inputs of the signal processing unit to alternately obtain biopotential signals from different portions of the head of the subject.

6. The system of claim 5 further including signal sensing means and wherein the switch arrangement includes control means for operating said switch arrangement responsive to signal properties sensed by said sensing means.

7. The system of claim 1 wherein the switch arrangement comprises a plurality of operators for moving the switch arrangement to a desired configuration.

8. The system of claim 1 or 2 wherein said signal processing unit comprises a differential amplifier having a positive signal input, a negative signal input, and a ground input.

9. The system of claim 1 further defined as an EEG sensor system for obtaining neurological biopotential signals from the brain of the subject and wherein said connection means receives electrical signals from the brain transmitted through the array.

10. The system of claim 9 wherein the switch arrangement is capable of directing the signals from the electrode array to the first, second, and third inputs in a configuration to obtain signals from a selected portion of the brain.

11. The system of claim 9 wherein the switch arrangement is capable of directing the signals from the electrode array to the inputs of the signal processing unit in a configuration to obtain biopotential signals from the overall frontal area of the forebrain.

12. The system of claim 9 wherein the switch arrangement includes control means for operating the switching arrangement to alternately direct the signals from the electrode array to the inputs of the signal processing unit to alternately obtain neurological biopotential signals from different portions of the brain.

13. The system of claim 12 further including signal sensing means and wherein the switch arrangement includes control means for operating said switch arrangement responsive to signal properties sensed by said sensing means.

14. The system of claim 9 wherein said signal processing unit comprises a differential amplifier having a positive signal input, a negative signal input, and a ground input.

15. A system of claim 1, 2 or 9 further including a three electrode array comprising:
 a) a central electrode array body including a first electrode and a first conductor extending from the first electrode, said first electrode being positionable at a first desired location on the subject;
 b) a first electrode array side body including a second electrode and a second conductor extending from the second electrode, said second electrode being positionable at a second desired location on the subject at a distance from said first location, the locations and distance being related to a first portion of the head of the subject; and
 c) a second electrode array side body including a third electrode and a third conductor extending from the third electrode, said third electrode being positionable at a third desired location on the subject at a distance from said first location, the locations and distance being related to a second portion of the head of the subject;
 the conductors being couplable to said connection means.

16. A method for utilizing an electrode array to measure activity in the head of a subject that produces biopotential signals, the method comprising the steps of:
 a) placing an electrode array on the head of the subject, the array including a centrally located first electrode, a second electrode positioned to one side of the centrally located first electrode, and a third electrode positioned on an opposite side of the centrally located first electrode with respect to said second electrode, said first, second, and third electrodes receiving biopotential signals;
 b) connecting inputs of first, second, and third switch elements of a configurable switch arrangement to each of the first, second, and third electrodes;
 c) connecting an output of each of the switch elements to one of a first, second, or third input of a signal processing unit; and
 d) selecting a configuration of the switch arrangement to direct signals received by the first, second and third electrodes to desired ones of the first, second, and third inputs to generate an output signal indicative of the activity in a desired portion of the head of the subject.

17. The method of claim 16 wherein the step of selecting the configuration of the switch arrangement comprises the step of operating a common actuator for the switch elements of said switch arrangement.

18. The method of claim 16 further comprising the step of providing a display from the output signal of an output signal device.

19. The method of claim 16 wherein the signal processing unit comprises a differential amplifier signal device having a positive signal input, a negative signal input and a ground input.

20. The method of claim 16 further defined as a method for measuring neurological activity in the brain of the subject, and wherein step (d) is further defined as selecting a configuration of the switch arrangement to generate an output signal indicative of the neurological activity in a desired portion of the brain of the subject.

21. The method of claim 20 wherein the desired portion of the brain is the right hemisphere of the forebrain.

22. The method of claim 20 wherein the desired portion of the brain is a left hemisphere of the forebrain.

23. The method of claim 20 wherein the desired portion of the brain is the overall frontal cortex of the brain.

24. The method of claim 16 further defined as a method for measuring biopotential activity arising from muscle activity of the subject, and wherein step (d) is further defined as selecting a configuration of the switch arrangement to generate an output signal indicative of the muscle activity in a desired portion of the head of the subject.

25. The method of claim 16 further comprising the step of:
 a) altering the configuration of the switch arrangement and the inputs to the signal processing unit to provide an output signal indicative of the activity in a further desired portion of the head.

26. The method of claim 25 wherein the step of altering the configuration of the switch arrangement is carried out automatically.

27. The method of claim 25 further including the step of sensing properties of the electrode signals and wherein the step of altering the configuration of the switch arrangement is further defined as carrying out the alteration responsive to the sensed signal properties.

28. The method of claim 25 wherein the step of altering the configuration of the switch arrangement is further defined as carrying out the alteration in a manner to optimize the signal to noise ratio in the output signal.

* * * * *